United States Patent
Swanson

(10) Patent No.: US 7,357,800 B2
(45) Date of Patent: Apr. 15, 2008

(54) POWER SUPPLY AND CONTROL APPARATUS AND ELECTROPHYSIOLOGY SYSTEMS INCLUDING THE SAME

(75) Inventor: David K. Swanson, Campbell, CA (US)

(73) Assignee: Boston Scientific Scimed, Inc.

( * ) Notice: Subject to any disclaimer, the term of this patent is extended or adjusted under 35 U.S.C. 154(b) by 733 days.

(21) Appl. No.: 10/368,108

(22) Filed: Feb. 14, 2003

(65) Prior Publication Data

US 2004/0162556 A1  Aug. 19, 2004

(51) Int. Cl.
*A61B 18/12* (2006.01)
(52) U.S. Cl. .................... 606/39; 128/898; 606/34
(58) Field of Classification Search ........... 606/28–52; 607/101–103, 115, 121, 122, 116
See application file for complete search history.

(56) References Cited

U.S. PATENT DOCUMENTS

| | | | |
|---|---|---|---|
| 4,685,459 A | 8/1987 | Koch | |
| 5,342,357 A | 8/1994 | Nardella | |
| 5,348,554 A | 9/1994 | Imran et al. | |
| 5,403,311 A | 4/1995 | Abele et al. | |
| 5,456,682 A | 10/1995 | Edwards et al. | |
| 5,496,312 A | 3/1996 | Klicek | |
| 5,562,720 A | 10/1996 | Stern et al. | |
| 5,575,810 A | 11/1996 | Swanson | |
| 5,582,609 A * | 12/1996 | Swanson et al. | 606/39 |
| 5,673,695 A * | 10/1997 | McGee et al. | 600/374 |
| 5,697,536 A | 12/1997 | Eggers et al. | |
| 5,702,386 A | 12/1997 | Stern et al. | |
| 5,755,715 A | 5/1998 | Stern et al. | |
| 5,759,158 A | 6/1998 | Swanson | |
| 5,837,001 A | 11/1998 | Mackey | |
| 5,871,523 A * | 2/1999 | Fleischman et al. | 607/99 |
| 5,935,079 A | 8/1999 | Swanson et al. | |
| 5,954,686 A * | 9/1999 | Garito et al. | 604/37 |
| 5,961,513 A | 10/1999 | Swanson | |
| 6,050,996 A | 4/2000 | Schmaltz | |
| 6,056,747 A | 5/2000 | Saadat | |
| 6,063,078 A | 5/2000 | Wittkampf | |
| 6,096,037 A | 8/2000 | Mulier et al. | |
| 6,142,994 A | 11/2000 | Swanson et al. | |
| 6,146,379 A * | 11/2000 | Fleischman et al. | 606/41 |
| 6,171,305 B1 | 1/2001 | Sherman | |
| 6,183,468 B1 | 2/2001 | Swanson et al. | |
| 6,200,314 B1 | 3/2001 | Sherman | |
| 6,237,604 B1 | 5/2001 | Burnside et al. | |
| 6,245,068 B1 | 6/2001 | Olson | |

(Continued)

FOREIGN PATENT DOCUMENTS

EP    0694291 A1    1/1996

(Continued)

OTHER PUBLICATIONS

PCT International Search Report dated Aug. 4, 2004 for PCT application No. PCT/US2004/003612.

(Continued)

*Primary Examiner*—Henry M. Johnson, III
(74) *Attorney, Agent, or Firm*—Vista IP Lawgroup LLP

(57) ABSTRACT

A power supply and control apparatus operable in a bipolar mode, a unipolar mode, and a combined bipolar/unipolar mode.

31 Claims, 5 Drawing Sheets

U.S. PATENT DOCUMENTS

| | | |
|---|---|---|
| 6,273,887 B1 | 8/2001 | Yamauchi |
| 6,312,425 B1 | 11/2001 | Simpson |
| 6,319,249 B1 | 11/2001 | Tollner |
| 6,346,104 B2 | 2/2002 | Daly et al. |
| 6,421,556 B2 | 7/2002 | Swanson |
| 6,464,700 B1 | 10/2002 | Koblish et al. |
| 6,471,699 B1 | 10/2002 | Fleischman |
| 6,485,487 B1 | 11/2002 | Sherman |
| 6,488,680 B1 | 12/2002 | Francischelli |
| 6,494,880 B1 | 12/2002 | Swanson et al. |
| 6,652,514 B2 * | 11/2003 | Ellman et al. ............... 606/37 |
| 6,692,491 B1 | 2/2004 | Phan |
| 7,115,122 B1 * | 10/2006 | Swanson et al. ............. 606/41 |
| 2001/0001314 A1 | 5/2001 | Davison |
| 2001/0025177 A1 | 9/2001 | Woloszko |
| 2002/0026187 A1 | 2/2002 | Swanson |
| 2002/0099428 A1 | 7/2002 | Kaufman |
| 2002/0120267 A1 | 8/2002 | Phan |
| 2003/0097126 A1 | 5/2003 | Woloszko |
| 2003/0158549 A1 | 8/2003 | Swanson |
| 2003/0212444 A1 | 11/2003 | Truckai |
| 2004/0059325 A1 | 3/2004 | Swanson |
| 2005/0019653 A1 | 1/2005 | Dahlberg |
| 2005/0203499 A1 | 9/2005 | Pendekati |
| 2006/0047277 A1 | 3/2006 | Eberl |

FOREIGN PATENT DOCUMENTS

| | | |
|---|---|---|
| EP | 1557129 A1 | 8/1996 |
| EP | 0856291 A2 | 1/1998 |
| WO | WO 01/72234 A1 | 10/2001 |

OTHER PUBLICATIONS

PCT International Search Report forms PCT/ISA/220 and PCT/ISA/210, dated May 31, 2006, for International Application No. PCT/US2006/003268, Applicant Boston Scientific Scimed, Inc. (7 pages).

Written Opinion of the International Searching Authority, PCT International Search Report, PCT/ISA form 237, mailed May 31, 2006, for International Application No. PCT/US2006/003268, Applicant Boston Scientific Scimed, Inc. (5 pages).

Notice of Allowance dated May 10, 2006 for U.S. Appl. No. 10/255,025, filed Sep. 24, 2002 (4 pages).

Amendment dated Apr. 28, 2006 for U.S. Appl. No. 10/255,025, filed Sep. 24, 2002 (8 pages).

Final Office Action dated Feb. 14, 2006 for U.S. Appl. No. 10/255,025, filed Sep. 24, 2002 (11 pages).

Amendment dated Dec. 3, 2005 for U.S. Appl. No. 10/255,025, filed Sep. 24, 2002 (19 pages).

Declaration of Dr. David K. Swanson Under § 132 dated Nov. 22, 2005 for U.S. Appl. No. 10/255,025, filed Sep. 24, 2002 (3 pages).

Non-Final Office Action dated Jul. 13, 2005 for U.S. Appl. No. 10/255,025, filed Sep. 24, 2002 (9 pages).

Advisory Action dated Apr. 11, 2005 for U.S. Appl. No. 10/255,025, filed Sep. 24, 2002 (2 pages).

Amendment dated Mar. 14, 2005 for U.S. Appl. No. 10/255,025, filed Sep. 24, 2002 (20 pages).

Final Office Action dated Dec. 7, 2004 for U.S. Appl. No. 10/255,025, filed Sep. 24, 2002 (10 pages).

Amendment dated Sep. 28, 2004 for U.S. Appl. No. 10/255,025, filed Sep. 24, 2002 (16 pages).

Non-Final Office Action dated Jul. 19, 2004 for U.S. Appl. No. 10/255,025, filed Sep. 24, 2002 (8 pages).

PCT International Search Report forms PCT/ISA/220 and PCT/ISA/210, dated Jan. 1, 2004, for International Application No. PCT/US03/29270, Applicant Scimed Life Systems, Inc. (10 pages).

Communication under Rule 51(4) EPC, EPO Form 2004, for EP patent application 03756823.5, dated Aug. 8, 2005, Applicant Boston Scientific Limited, (6 pages).

EP Communication of a Notice of Opposition, EPO form 2300, for EP patent application 03756823.5, dated Nov. 29, 2006 and Opposition dated Nov. 22, 2006, Applicant Boston Scientific Limited, (15 pages).

Response to Opposition against EP patent application 03756823.5 dated Nov. 22, 2006; Response submitted Jun. 19, 2007, Applicant Boston Scientific Limited, (7 pages).

Non-Final Office Action dated Sep. 24, 2007 for U.S. Appl. No. 10/255,025, filed Sep. 24, 2002 (7 pages).

International Preliminary Report on Patentability for PCT/US2006/003268, forms PCT/IB/326, PCT/IB/373 and PCT/ISA/237 mailed Nov. 1, 2007, Applicant Boston Scientific Limited, (7 pages).

* cited by examiner

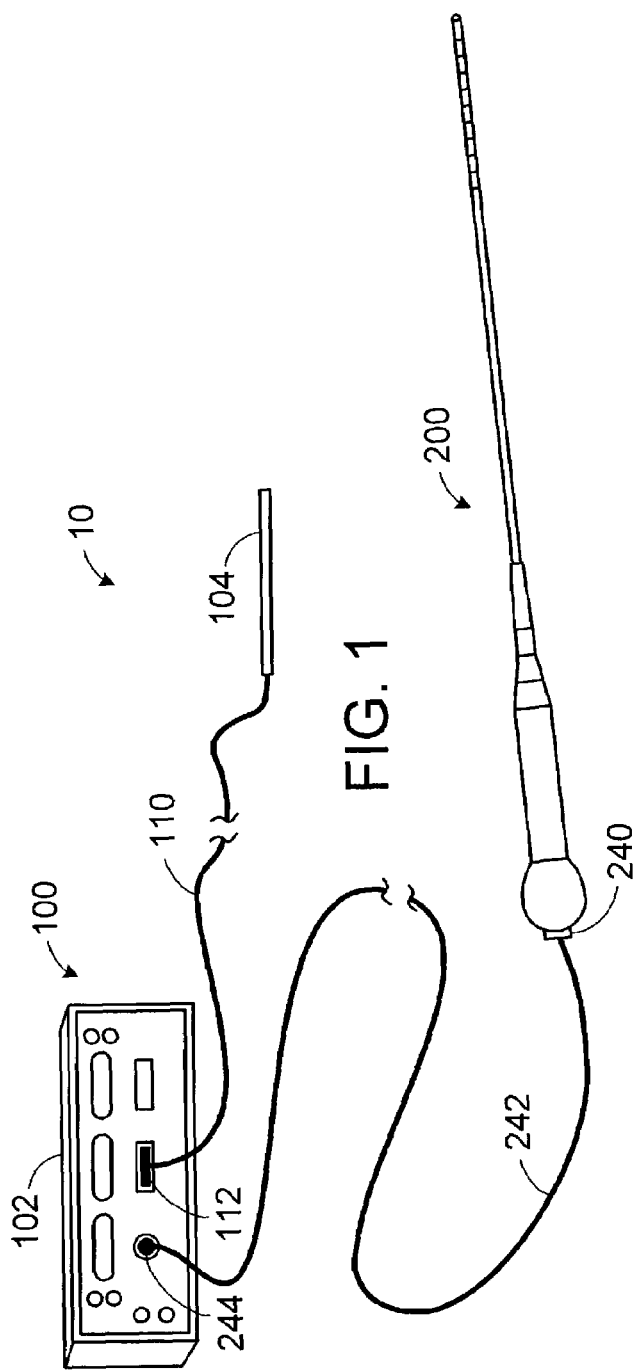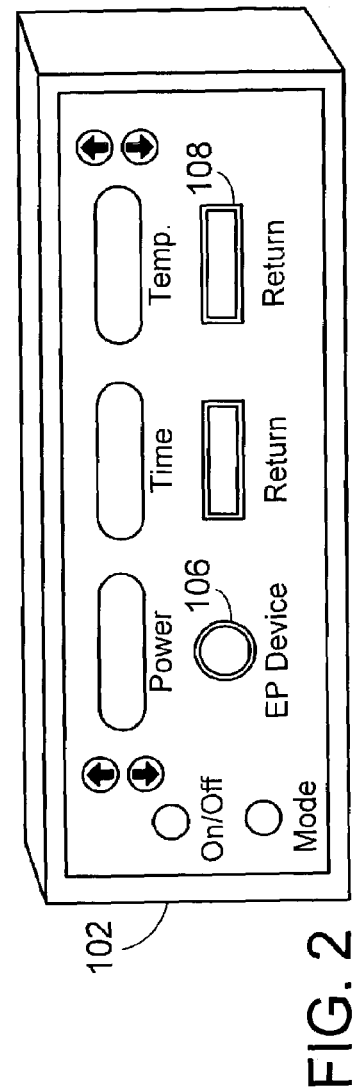
FIG. 1
FIG. 2

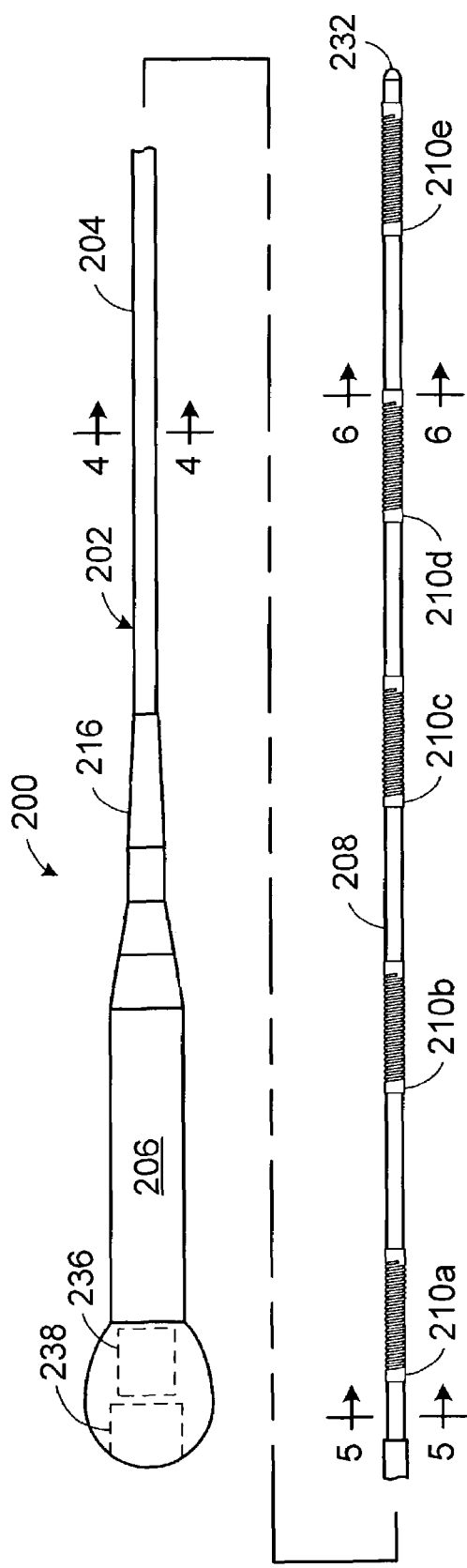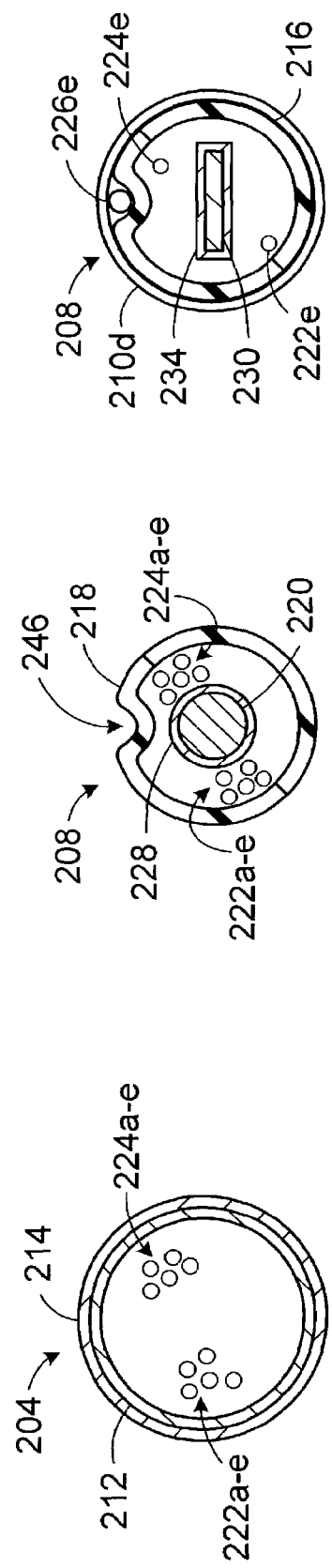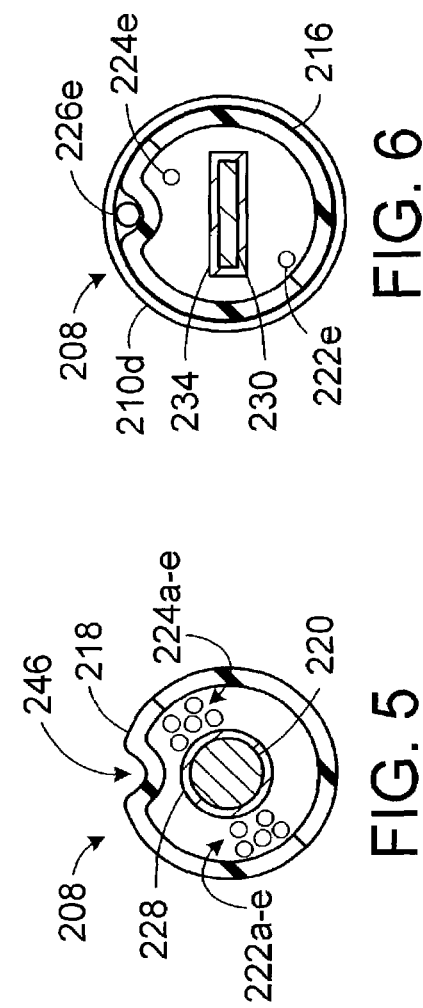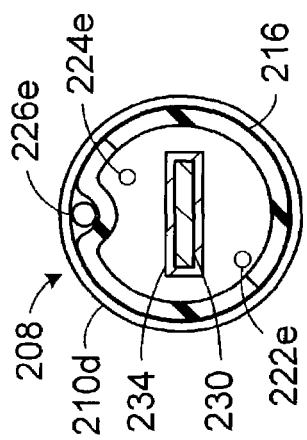

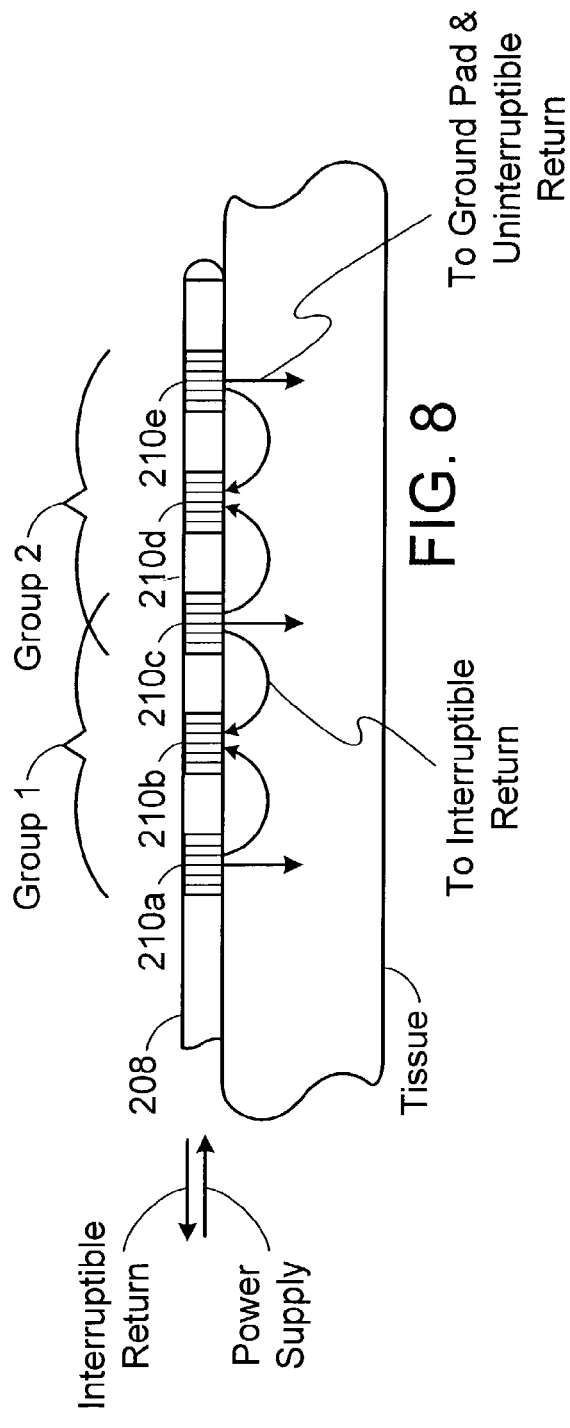
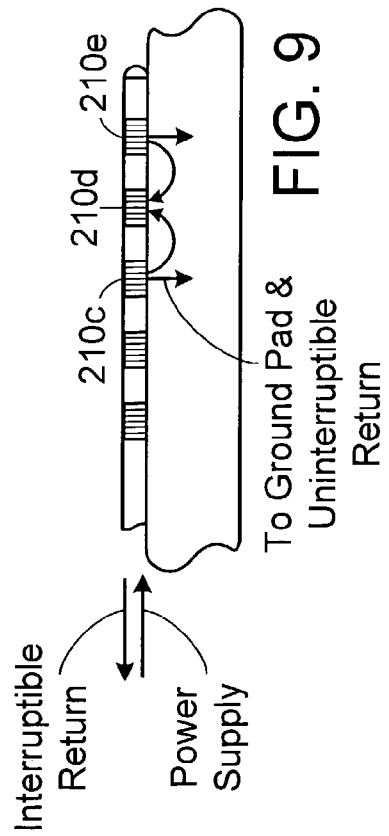

POWER SUPPLY AND CONTROL APPARATUS AND ELECTROPHYSIOLOGY SYSTEMS INCLUDING THE SAME

BACKGROUND OF THE INVENTIONS

1. Field of Inventions

The present inventions relate generally to electrophysiology systems.

2. Description of the Related Art

There are many instances where therapeutic elements must be inserted into the body. One instance involves the formation of therapeutic lesions to the treat cardiac conditions such as atrial fibrillation, atrial flutter and arrhythmia. Therapeutic lesions may also be used to treat conditions in other regions of the body including, but not limited to, the prostate, liver, brain, gall bladder, uterus and other solid organs. Typically, the lesions are formed by ablating tissue with one or more electrodes. Electromagnetic radio frequency ("RF") energy applied by the electrode heats, and eventually kills (i.e. "ablates"), the tissue to form a lesion. During the ablation of soft tissue (i.e. tissue other than blood, bone and connective tissue), tissue coagulation occurs and it is the coagulation that kills the tissue. Thus, references to the ablation of soft tissue are necessarily references to soft tissue coagulation. "Tissue coagulation" is the process of cross-linking proteins in tissue to cause the tissue to jell. In soft tissue, it is the fluid within the tissue cell membranes that jells to kill the cells, thereby killing the tissue. Depending on the procedure, a variety of different electrophysiology probes may be used to position a plurality of electrodes at the target location.

Catheters, which are one type of electrophysiology probe used to create lesions, typically include a relatively long and relatively flexible body that has one or more electrodes on its distal portion. The portion of the catheter body that is inserted into the patient is typically from 23 to 55 inches in length and there may be another 8 to 15 inches, including a handle, outside the patient. The proximal end of the catheter body is connected to the handle which includes steering controls. In the case of cardiac conditions, the length and flexibility of the catheter body allow the catheter to be inserted into a main vein or artery (typically the femoral artery), directed into the interior of the heart, and then manipulated such that the electrodes contact the tissue that is to be ablated. Fluoroscopic imaging is used to provide the physician with a visual indication of the location of the catheter. Exemplary catheters are disclosed in U.S. Pat. Nos. 5,582,609 and 6,287,301.

Surgical probes, which are another type of electrophysiology probe used to create lesions, often include a handle, a relatively short shaft that is from 4 inches to 18 inches in length and either rigid or relatively stiff, and a distal section that is from 1 inch to 10 inches in length and either malleable or somewhat flexible. One or more electrodes are carried by the distal section. In the case of cardiac conditions, surgical probes may be used in epicardial and endocardial procedures, including open heart procedures and minimally invasive procedures where access to the heart is obtained via a thoracotomy, thoracostomy or median sternotomy. Exemplary surgical probes are disclosed in U.S. Pat. No. 6,142,994.

Electrophysiology probes receive power from power supply and control apparatus (also referred to as "electrosurgical units"). The power supply and control apparatus typically monitor tissue temperature through the use of temperature sensors that are carried by the probes. Monitoring tissue temperature and controlling power based on tissue temperature insures that lesions are created (soft tissue coagulation occurs at 50° C.) without over-heating tissue and causing coagulum and charring (over-heating occurs at 100° C.). The electrodes and temperature sensors are connected to the power supply and control apparatus by wires that extend through the interior of the probes. Relatively long electrodes may include a pair of power wires and/or a pair of temperature sensors.

Conventional power supply and control apparatus operate in either a unipolar mode or a bipolar mode. In the unipolar mode, the ablation energy emitted by the electrodes is returned to the power supply and control apparatus through a grounding pad (also referred to as an "indifferent electrode" or a "back plate" or "return electrode") that is externally attached to the skin of the patient. Power may be controlled on an electrode-by-electrode basis based on the tissue temperatures measured at each of the electrodes. Turning to the bipolar mode, energy that is transmitted to tissue by one or more electrodes is returned to the power supply and control apparatus through one or more return electrodes on the probe. At best, power may be controlled on a "electrode pair-by-electrode pair" basis where one transmitting electrode and one return electrode define a pair. Power is supplied to the transmitting electrode based on the highest temperature measured at the electrodes in the pair.

The inventor herein has determined that, regardless of the type of electrophysiology probe which is used, conventional apparatus and methods for forming therapeutic lesions are susceptible to improvement. For example, the number of electrodes that may be carried by a probe tends to be limited by the number of power and temperature control wires that can be accommodated by the interior of the probe. The inventor herein has also determined that, in the case of unipolar coagulation, the fact that the electrodes have to be relatively close to one another to form continuous lesions, coupled with the aforementioned inherent limitations on the number of electrodes, limits the overall length of the lesions that may be produced by the probes. The inventor herein has further determined that, although the electrodes may be positioned farther apart in the case of bipolar coagulation, the lack of individual electrode control (or "electrode-by-electrode control") in conventional bipolar systems limits the physician's ability to precisely control lesion length.

SUMMARY OF THE INVENTIONS

A power supply and control apparatus in accordance with a present invention is operable in a unipolar mode and a combined bipolar/unipolar mode. In a preferred implementation, the power supply and control apparatus will switch from the combined bipolar/unipolar mode to the unipolar mode in response to the measurement of a tissue coagulation variable value.

Such an apparatus provides a number of advantages over conventional power supply and control apparatus. The following example of a three electrode probe may be used to illustrate some of these advantages. When operating in the combined bipolar/unipolar mode, the proximal and distal electrodes on the probe will be used to transmit energy to tissue and the electrode between the transmitting electrodes will act as a return electrode. A grounding pad will also be used and, although the majority of power from the transmitting electrodes will be returned to a power return line in the power supply and control apparatus by way of the return electrode on the probe, a smaller amount of power will be returned to the power return line by way of the grounding pad. As such, coagulation procedures will proceed in a manner similar to bipolar coagulation when the apparatus is operating in the combined bipolar/unipolar mode. This allows the electrodes to be spaced relatively far apart, as compared to probes that are designed to operate primarily in the unipolar mode, thereby facilitating the creation of longer lesions for a given number of electrodes.

The level of power to the transmitting electrodes will preferably be controlled on an electrode-by-electrode basis based on a tissue coagulation variable associated with the transmitting electrodes such as, for example, the respective temperatures measured at the transmitting electrodes. This insures that the tissue associated with the transmitting electrodes will be ablated without over-heating the tissue and causing coagulum and charring.

The present apparatus also controls the flow of energy through the return electrode based on a tissue coagulation variable associated with the return electrode such as, for example, the temperature measured at the return electrode. Given that the return electrode is receiving power from two transmitting electrodes, the higher current densities at the return electrode will result in higher temperatures at the return electrode than at the transmitting electrodes. When the temperature exceeds a predetermined level, the power supply and control apparatus will disconnect the return electrode from the power return line to interrupt the flow of power through the return electrode. This allows the return electrode to cool. The transmitting electrodes will continue to transmit energy to the tissue and, because power flow through the return electrode has been interrupted, the power will be returned to the power supply and control apparatus by way of the grounding pad. At this point, the apparatus is operating in a unipolar mode. Once it has sufficiently cooled, the return electrode will be reconnected to the power return line, thereby reinitiating the flow of energy therethrough, and the apparatus will return to the combined bipolar/unipolar mode.

As illustrated in the example above, the present power supply and control apparatus individually controls tissue coagulation at the transmitting electrodes by adjusting the level of energy that passes through the transmitting electrodes and individually controls tissue coagulation at the return electrode by selectively interrupting the flow of energy through the return electrode. The present power supply and control apparatus, therefore, provides the spacing benefits heretofore only associated with bipolar ablation in addition to the individual electrode control heretofore only associated with unipolar ablation.

The above described and many other features and attendant advantages of the present inventions, which also include electrophysiology systems that incorporate the aforementioned power supply and control apparatus, will become apparent as the inventions become better understood by reference to the following detailed description when considered in conjunction with the accompanying drawings.

BRIEF DESCRIPTION OF THE DRAWINGS

Detailed description of preferred embodiments of the inventions will be made with reference to the accompanying drawings.

FIG. 1 is a perspective view of an electrophysiology system in accordance with a preferred embodiment of a present invention.

FIG. 2 is a front perspective view of an electrosurgical unit in accordance with a preferred embodiment of a present invention.

FIG. 3 is a plan view of a surgical probe in accordance with a preferred embodiment of a present invention.

FIG. 4 is a section view taken along line 4-4 in FIG. 3.

FIG. 5 is a section view taken along line 5-5 in FIG. 3.

FIG. 6 is a section view taken along line 6-6 in FIG. 3.

FIG. 8 is a side view of a tissue coagulation procedure in accordance with a preferred embodiment of a present invention.

FIG. 9 is a side view of a tissue coagulation procedure in accordance with a preferred embodiment of a present invention.

FIG. 10 is a side view of a tissue coagulation procedure in accordance with a preferred embodiment of a present invention.

DETAILED DESCRIPTION OF THE PREFERRED EMBODIMENTS

Figure 7:
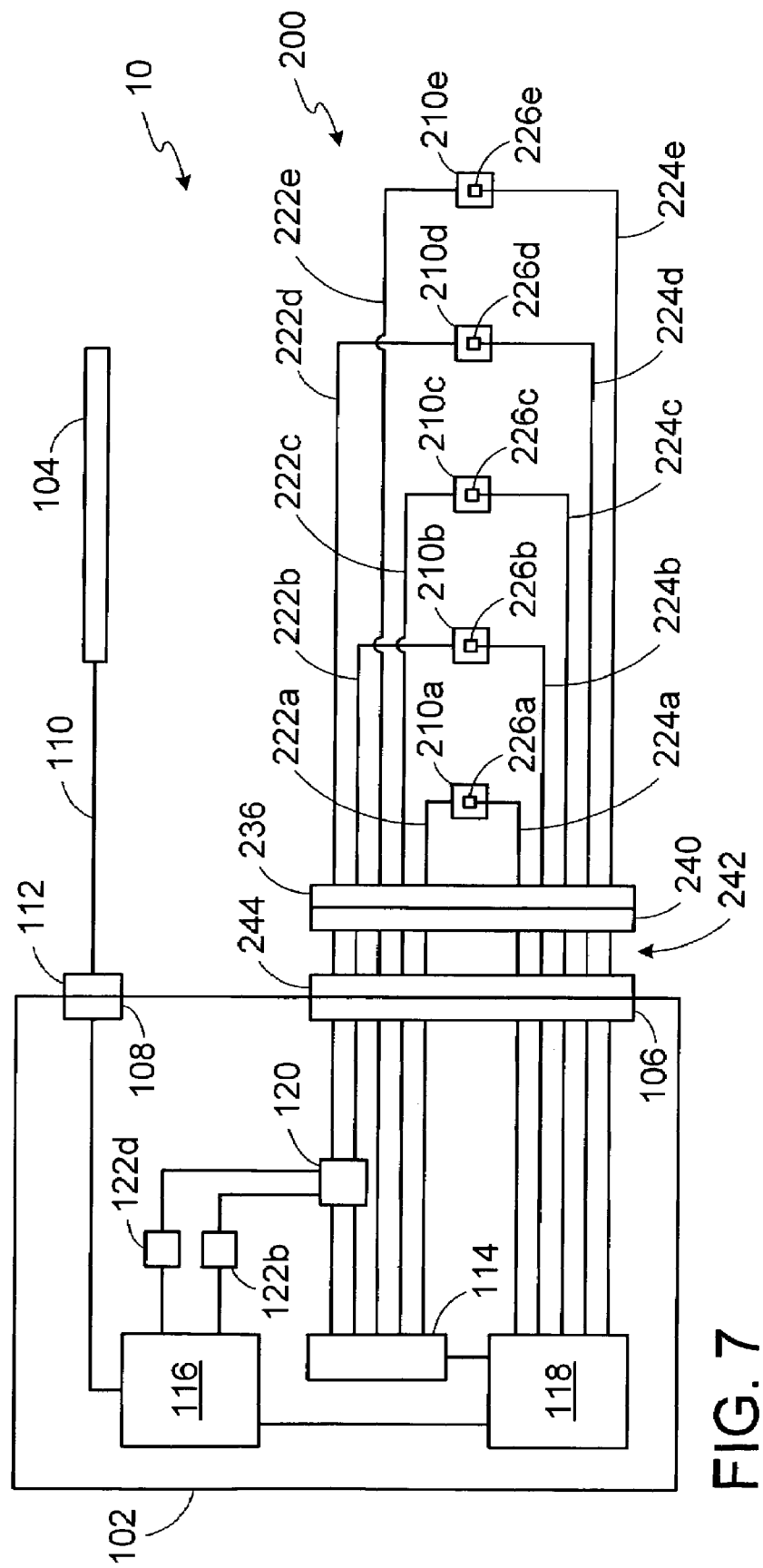
FIG. 7 is a diagrammatic view of an electrophysiology system in accordance with a preferred embodiment of a present invention.

The following is a detailed description of the best presently known modes of carrying out the inventions. This description is not to be taken in a limiting sense, but is made merely for the purpose of illustrating the general principles of the inventions.

The detailed description of the preferred embodiments is organized as follows:
  I. Introduction
  II. Exemplary Electrophysiology System
  III. Temperature Sensing and Power Control The section titles and overall organization of the present detailed description are for the purpose of convenience only and are not intended to limit the present inventions.

I. Introduction

Electrophysiology systems in accordance with the present inventions include a device that carries a plurality of electrodes and a control system that supplies and controls power to the electrodes in a combined bipolar/unipolar mode. Although not limited to any particular type of device, electrophysiology systems in accordance with the present inventions may, for example, be provided with a hand held surgical device (or "surgical probe") such as the ThermalLine™ and Cobra® surgical probes from EP Technologies, Inc. in San Jose, Calif. The electrodes on the distal end of the probe shaft may be placed directly in contact with the targeted tissue area by a physician during a surgical procedure, such as open heart surgery. Here, access may be obtained by way of a thoracotomy, median sternotomy, or thoracostomy. Alternatively, electrophysiology systems in accordance with the present inventions may be provided with a catheter, such as the MECA™ catheter from EP Technologies, Inc. Catheters may be used within body lumens, chambers or cavities for diagnostic or therapeutic purposes in those instances where access to interior bodily regions is obtained through, for example, the vascular system or alimentary canal and without complex invasive surgical procedures. Electrophysiology clamps are another example of a device for which the present inventions have application.

The present inventions also have a wide variety of treatment applications. For example, the present inventions are useful in the treatment of arrhythmia conditions within the heart and are designed to produce intimate tissue contact with target substrates associated with various arrhythmias, namely atrial fibrillation, atrial flutter, and ventricular tachycardia. The inventions herein also have application in the treatment of ailments of the gastrointestinal tract, prostrate, brain, gall bladder, uterus, and other regions of the body.

II. Exemplary Electrophysiology System

As illustrated for example in FIGS. 1 and 2, an exemplary electrophysiology system 10 in accordance with a preferred embodiment of a present invention includes a power supply and control system 100 and a surgical probe 200. The power supply and control system 100 includes an electrosurgical unit (or "ESU") 102, which supplies and controls energy to the surgical probe 200, and a grounding pad 104, which returns energy to the ESU. To that end, the exemplary ESU 102 is provided with a power connector 106 and a pair of return connectors 108. The exemplary power and return connectors 106 and 108 have different shapes to avoid confusion. The ESU 102 also includes a plurality of displays and buttons that are used to set the level of power supplied to the surgical probe 200, the temperature at the probe electrodes and the length of time that the power will be transmitted. The exemplary ESU 102 has three modes of operation—(1) unipolar, (2) bipolar and (3) combined bipolar/unipolar—and is discussed in greater detail in Section III below.

Turning to FIGS. 3-6, the surgical probe 200 in the exemplary system 10 includes a relatively short shaft 202 with a proximal section 204, which is connected to a handle 206, and a distal section 208, on which electrodes 210a-e are supported. The shaft proximal section 204 consists of a hypotube 212, which is either rigid or relatively stiff, and an outer polymer tubing 214 over the hypotube. The handle 206 preferably consists of two molded handle halves and is provided with strain relief element 216. The shaft proximal section 204 in the illustrated embodiment may be from 4 inches to 18 inches in length and is preferably 6 inches to 8 inches. The shaft distal section 208, which is preferably either malleable, somewhat flexible or some combination thereof, may be from 1 inch to 10 inches in length and is preferably 2 to 3 inches.

As used herein the phrase "relatively stiff" means that the shaft (or distal section or other structural element) is either rigid, malleable, or somewhat flexible. A rigid shaft cannot be bent. A malleable shaft is a shaft that can be readily bent by the physician to a desired shape, without springing back when released, so that it will remain in that shape during the surgical procedure. Thus, the stiffness of a malleable shaft must be low enough to allow the shaft to be bent, but high enough to resist bending when the forces associated with a surgical procedure are applied to the shaft. A somewhat flexible shaft will bend and spring back when released. However, the force required to bend the shaft must be substantial. Rigid and somewhat flexible shafts are preferably formed from stainless steel, while malleable shafts are formed from annealed stainless steel., Additional information concerning "relatively stiff" shafts is provided in U.S. Pat. No. 6,142,994, which is incorporated herein by reference.

In those instances where a malleable shaft proximal portion 204 is desired, the hypotube 212 may be a heat treated malleable hypotube. By selectively heat treating certain portions of the hypotube, one section of the hypotube can be made more malleable than the other. The outer tubing 214 may be formed from Pebax® material, polyurethane, or other suitable materials.

As noted above, the shaft distal section 208 can be either somewhat flexible, in that it will conform to a surface against which it is pressed and then spring back to its original shape when removed from the surface, malleable, or some combination thereof. A bending modulus of between 3 lb.-in.$^2$ and 50 lb.-in.$^2$ is preferred. In the exemplary implementation illustrated in FIGS. 3-6, the distal section 208 includes a malleable proximal portion and a flexible distal portion. Although the relative lengths of the portions may vary to suit particular applications, the malleable proximal portion and a flexible distal portion are equal in length in the illustrated embodiment.

Referring more specifically to FIGS. 5 and 6, the exemplary shaft distal section 208 includes an outer member 218 that carries the electrodes 210a-e. The outer member 218 is a flexible tubular structure which has an outer diameter that is, depending on the diameter of the electrodes 210a-e, typically between about 2 mm and about 4 mm. The outer member 218 in the illustrated embodiment, which is intended for use in cardiovascular applications, typically has an outer diameter of about 3 mm. Suitable support structure materials include, for example, flexible biocompatible thermoplastic tubing such as unbraided Pebax® material, polyethylene, or polyurethane tubing.

Turning to the interior of the shaft distal section 208, the exemplary malleable portion includes a mandrel 220 made of a suitably malleable material, such as annealed stainless steel or beryllium copper, that may be fixed directly within the distal end of the shaft's hypotube 212 and secured by, for example, soldering, spot welding or adhesives. Sufficient space should be provided to allow passage of the power lines 222a-e, which are connected to the electrodes 210a-e, and the temperature sensor signal lines 224a-e to temperature sensors 226a-e (FIGS. 6 and 7) such as thermocouples or thermistors. As described in greater detail below, the power lines 222a-e may be used to transmit energy from the ESU 102 to the electrodes 210a-e, or used to return energy transmitted by the electrodes to the ESU, or not used at all, depending on the mode of operation. An insulating sleeve 228 is placed over the mandrel 216 to protect the power lines 222a-e and temperature sensor signal lines 224a-e. The insulating sleeve 228 is preferably formed from Pebax® material, polyurethane, or other suitable materials.

With respect to the flexible portion, a spring member 230, which is preferably either a solid flat wire spring (as shown), a round wire, or a three leaf flat wire Nitinol spring, is connected to the distal end of the mandrel 220 with a crimp tube or other suitable instrumentality. The distal end of the spring member 230 is connected to a tip member 232 by, for example, soldering, spot welding or adhesives. The tip member 232 is also secured to the distal end of the outer member 218. Other spring members, formed from materials such as 17-7 or carpenter's steel, may also be used. The spring member 230 is also enclosed within the insulating sleeve 234. The spring member 230 may be pre-stressed so that the distal tip is pre-bent into a desired shape. Additional details concerning distal sections that have a malleable proximal portion and a flexible distal portion are provided in U.S. Pat. No. 6,464,700, which is incorporated herein by reference.

In an alternative configuration, the distal section 208 may be formed by a hypotube that is simply a continuation of the shaft hypotube 212 covered by a continuation of the outer tubing 214. However, the distal end hypotube can also be a separate element connected to the shaft hypotube 212, if it is desired that the distal end hypotube have different stiffness (or bending) properties than the shaft hypotube. It should also be noted that the distal section 208 may be made malleable from end to end by eliminating the spring member 230 and extending the malleable mandrel 220 to the tip member 232. Conversely, the distal section 208 may be made flexible from end to end by eliminating the malleable mandrel 220 and extending the spring member 230 from the hypotube 212 to the tip member 232.

With respect to the connection of the grounding pad 104 and surgical probe 200 to the ESU 102, and referring to FIGS. 1-3, the grounding pad is provided with a cable 110 and a connector 112 that is configured to be received by one of the return connectors 108 on the ESU. The power lines 222a-e and temperature sensor signal lines 224a-e for the electrodes 210a-e and temperature sensors 226a-e on the surgical probe 200 are connected to a PC board 236 in the handle 206. The handle also includes a port 238 that is configured to receive a connector 240 from a cable 242. The cable 242 also includes a connector 244 that may be connected to the power connector 106 on the ESU 102.

Turning to the configuration of the exemplary electrodes 210a-e, the electrodes are spiral (or "helical") coils that are relatively flexible and formed from electrically conducting material, like copper alloy, platinum, or stainless steel, or compositions such as drawn-filled tubing (e.g. a copper core with a platinum jacket). The electrically conducting material can be further coated with platinum-iridium or gold to improve its conduction properties and biocompatibility. An exemplary coil electrode configuration is disclosed in U.S. Pat. No. 5,797,905. With respect to the manufacture of a helical electrode, such an electrode may be manufactured by, for example, laser cutting a hypotube (as shown) or winding wire that is either round or rectangular in cross-section into the desired shape.

As an alternative, the electrodes may be in the form of solid rings of conductive material, like platinum, or can comprise a conductive material, like platinum-iridium or gold, coated upon an underlying non-conductive support member using conventional coating techniques or an ion beam assisted deposition (IBAD) process. For better adherence, an undercoating of nickel or titanium can be applied. The electrodes can also be formed with a conductive ink compound that is pad printed onto an underlying non-conductive support member. A preferred conductive ink compound is a silver-based flexible adhesive conductive ink (polyurethane binder), however other metal-based adhesive conductive inks such as platinum-based, gold-based, copper-based, etc., may also be used to form electrodes. Such inks are more flexible than epoxy-based inks.

The exemplary electrodes 210a-e are preferably about 2 mm to about 18 mm in length with about 2 mm to about 10 mm spacing. In the preferred embodiment, the electrodes 210a-e are about 4 mm in length with about 5 mm spacing, which will result in the creation of continuous lesion patterns in tissue when coagulation energy is supplied to an electrode and returned by an adjacent electrode in the bipolar mode, or is supplied to an electrode and returned by an adjacent electrode and the grounding pad in the combined bipolar/unipolar mode. Here, the temperature sensors 226a-e will be positioned at the mid-point of the electrodes 210a-e. When longer electrodes are employed, there will preferably be two temperature sensors associated each of the electrodes, with one temperature sensor at each longitudinal end of the electrodes. For rigid electrodes, the length of the each electrode can vary from about 2 mm to about 10 mm. Using multiple rigid electrodes longer than about 10 mm each adversely effects the overall flexibility of the device, while electrodes having lengths of less than about 2 mm do not consistently form the desired continuous lesion patterns.

The portion of the electrodes 210a-e that are not intended to contact tissue (and be exposed to the blood pool) may be masked through a variety of techniques with a material that is preferably electrically and thermally insulating. This prevents the transmission of coagulation energy directly into the blood pool and directs the energy directly toward and into the tissue. For example, a layer of UV adhesive (or another adhesive) may be painted on preselected portions of the electrodes 210a-e to insulate the portions of the electrodes not intended to contact tissue. Deposition techniques may also be implemented to position a conductive surface only on those portions of the assembly intended to contact tissue. Alternatively, a coating may be formed by dipping the electrodes in PTFE material.

The electrodes 210a-e may also include a porous material coating, which transmits coagulation energy through an electrified ionic medium. For example, as disclosed in U.S. Pat. No. 5,991,650, electrodes and temperature sensors may be coated with regenerated cellulose, hydrogel or plastic having electrically conductive components. With respect to regenerated cellulose, the coating acts as a mechanical barrier between the surgical device components, such as electrodes, preventing ingress of blood cells, infectious agents, such as viruses and bacteria, and large biological molecules such as proteins, while providing electrical contact to the human body. The regenerated cellulose coating also acts as a biocompatible barrier between the device components and the human body, whereby the components can now be made from materials that are somewhat toxic (such as silver or copper).

As illustrated for example in FIGS. 5 and 6, the temperature sensors 226a-e in the exemplary implementation are located within a linear channel 246 that is formed in the distal member 208. The linear channel 246 insures that the temperature sensors will directly face the tissue and be arranged in linear fashion. The illustrated arrangement results in more accurate temperature readings which, in turn, results in better temperature control. As such, the actual tissue temperature will more accurately correspond to the temperature set by the physician on the power control device, thereby providing the physician with better control of the lesion creation process and reducing the likelihood that embolic materials will be formed.

Surgical probes and catheters in accordance with the present inventions may also be provided with apparatus that cools the tissue during tissue coagulation procedures. The tissue cooling apparatus disclosed herein employ conductive fluid to cool tissue during coagulation procedures. More specifically, and as described below and in U.S. application Ser. No. 09/761,981, which is entitled "Fluid Cooled Apparatus For Supporting Diagnostic And Therapeutic Elements In Contact With Tissue" and incorporated herein by reference, heat from the tissue being coagulated is transferred to ionic fluid to cool the tissue while energy is transferred from an electrode or other energy transmission device to the tissue through the fluid by way of ionic transport. Cooling tissue during a coagulation procedure facilitates the formation of lesions that are wider and deeper than those that could be realized with an otherwise identical device which lacks tissue cooling apparatus.

III. Temperature Sensing and Power Control

As illustrated for example in FIG. 7, the exemplary ESU 102 includes a power supply 114, power return line 116 (e.g. a floating common, separated from earth ground) and a system controller 118. As noted above, the ESU 102 has three modes of operation—(1) unipolar, (2) bipolar and (3) combined bipolar/unipolar. The ESU includes buttons (not shown) which allow the operator to select the electrodes that will be used in the selected mode. In the unipolar mode, tissue coagulation energy is supplied by the power supply 114 (typically about 5 to 150 w), emitted by one or more of the electrodes 210a-e, and returned to the power return line 116 by way of the grounding pad 104. In the bipolar mode, one or more (but not all) of the electrodes 210a-e on the probe 200 will be used to transmit tissue coagulation energy from the power supply 114 to the tissue. One or more of the non-transmitting electrodes 210a-e is used to return energy to the power return line. The grounding pad 104 is not used to return power in the bipolar mode. This may be accomplished by physically disconnecting the grounding pad 104 or by actuating a button (or other switch) on the power supply. In the combined bipolar/unipolar mode, which is discussed in greater detail below with reference to FIGS. 8-10, one or more (but not all) of the electrodes 210a-e will be used to transmit tissue coagulation energy from the power supply 114 to the tissue. The grounding pad 104 and one or more of the non-transmitting electrodes 210a-e will be used to return energy to the power return line 116.

In the exemplary implementation illustrated in FIG. 7, electrodes 210a, 210c and 210e are used as transmitting electrodes (i.e. electrodes that transmit energy to the tissue) in each mode. Electrodes 210b and 210d, on the other hand, may be used as transmitting electrodes in the unipolar mode and may be used as return electrodes in the bipolar and combined bipolar/unipolar modes. To that end, the ESU 102 includes a switching device 120 that is used to individually and selectively connect electrode 210b and/or electrode 210d to the power supply 114 or power return line 116. The ESU 102 is also provided with switching devices 122b and 122d that may be used to individually and selectively disconnect the electrodes 210b and 210d from the power return line 116 when the ESU is operating in the combined bi-polar/unipolar mode. Thus, the energy return paths for the electrodes 210b and 210d are interruptible. The energy return path for the grounding pad 104 is not interruptible.

ESUs, such as the exemplary ESU 102, are typically configured such that the current from the ground pad 104 is monitored for safety purposes. The tissue coagulation procedure will be automatically stopped if the current is over a predetermined level for a predetermined time (e.g. 1 ampere for 3 seconds). In order to prevent the current returning by way of electrodes 210b and 210d from effecting the measurement of the grounding pad current in the combined bipolar/unipolar mode, the connection of the electrodes 210b and 210d to the power return line 116 is made downstream from the point in the circuitry where current from the grounding pad 104 is monitored.

In order to insure that tissue is coagulated without overheating and causing coagulum and charring, tissue temperature at each of the electrodes 210a-e is individually measured by the temperature sensors 226a-e and monitored by the ESU controller 118 in each operating mode. This is sometimes referred to as "multi-channel control." Suitable power control schemes which control the level of power to the electrodes based on sensed temperatures and are especially well suited for surgical probes are disclosed in U.S. Pat. No. 6,183,468. Suitable power control schemes which control power to the electrodes based on sensed temperatures and are especially well suited for catheters are disclosed in U.S. Pat. Nos. 5,456,682, 5,582,609 and 5,755,715. Other power control information is provided in U.S. Pat. No. 6,237,604.

The exemplary ESU 102 operates in the following manner in the unipolar mode. Referring to FIG. 7, and assuming for example that the operator has selected electrodes 210c-e, the ESU controller 118 will cause the switching device 120 to connect electrode 210d to the power supply 114. The power supply 114 will then supply coagulation energy to the electrodes 210c-e, which is in turn transmitted to the tissue and returned to the ESU 102 by way of the grounding pad 104. The ESU controller 118 monitors the temperature measured by the temperature sensors 226c-e and adjusts the energy supplied to the electrodes 210c-e as needed on an electrode-by-electrode basis until the procedure is complete. The ESU controller also monitors the current from the grounding pad 104.

With respect to the bipolar mode, and assuming for example that the operator has chosen electrodes 210a and 210b, the ESU controller 118 will cause the switching device 120 to connect electrode 210b to the power return line 116. The power supply 114 will then supply coagulation energy to the electrode 210a, which is transmitted to the tissue and returned to the ESU 102 by way of the electrode 210b. The grounding pad 104 is disconnected from the ESU 102 when the power supply and control system 100 is operating in the bipolar mode. The ESU controller 118 monitors the temperature measured by the temperature sensors 226a and 226b and adjusts the energy supplied to electrodes 210a as needed until the procedure is complete. With respect to current, the exemplary ESU 102 is programmed to simply assume that the current being returned by way of electrode 210b is equal to the current being supplied to electrode 210a.

One example of the operation of the ESU 102 in the combined bipolar/unipolar mode is illustrated in FIGS. 8-11. Although the present inventions are not limited to a five electrode configuration or the exemplary grouping, the electrodes 210a-e are grouped in two groups for control purposes. Each group includes a pair of transmitting electrodes separated by a return electrode. Referring first to FIG. 8, group 1 includes electrodes 210a-c and group 2 includes electrodes 210c-e. Electrodes 210a, 210c and 210e are used as transmitting electrodes, electrodes 210b and 210d are used as interruptible return electrodes, and electrode 210c is a member of both group 1 and group 2. A third group of electrodes, if there was one, would include electrode 210e and two additional electrodes. The electrode groups may be operated separately or simultaneously. The grounding pad 104 is connected to the ESU 102 and is used as a non-interruptible return from the patient to the power return line 116 when the power supply and control system 100 is operating in the combined bipolar/unipolar mode.

Figure 11:
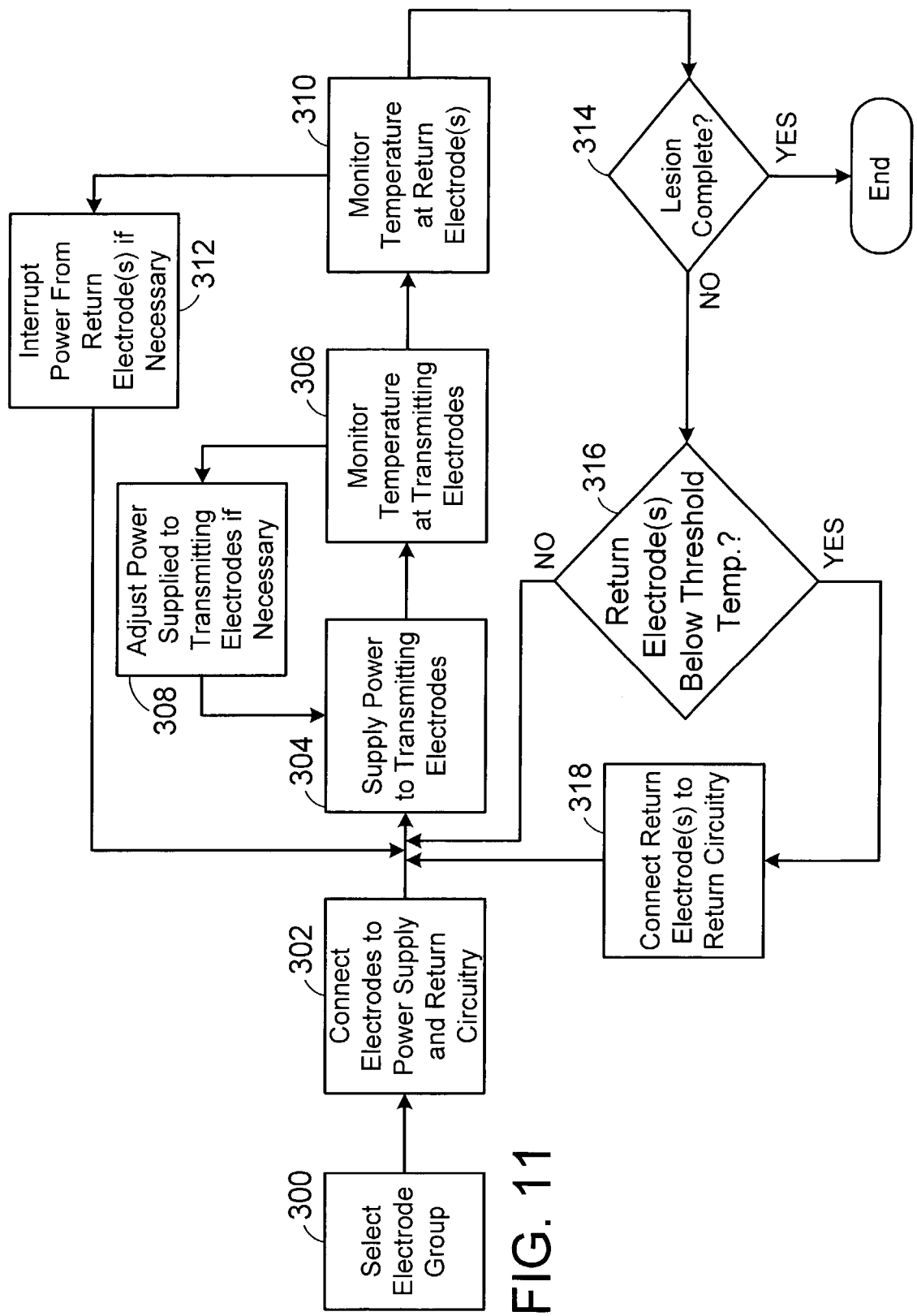
FIG. 11 is a flow chart of a combined bipolar/unipolar method in accordance with a preferred embodiment of the present invention.

Referring more specifically to FIGS. 9-11, and assuming for example that the operator has decided to form lesions with group 2 (Step 300), the ESU controller 118 will cause the switching devices 120, 122b and 122d to disconnect electrode 210b from the power return line 116 and to connect electrode 210d to the power return line (Step 302). The power supply 114 will then supply coagulation energy to electrodes 210c and 210e (Step 304), which is transmitted to the tissue. The majority of the energy is returned to the ESU 102 by way of the electrode 210d. A relatively smaller amount of current is returned to the ESU by way of the grounding pad. [Note FIG. 9.] The ESU controller 118 monitors the temperature measured by the temperature sensors 226c and 226e (Step 306) and adjusts the energy supplied to electrodes 210c and 210e as necessary until the procedure is complete (Step 308). The ESU controller 118 also monitors the temperature measured by temperature sensor 226d, which is associated with the return electrode 210d (Step 310). With respect to current, the exemplary ESU 102 is programmed to simply assume that the current being returned by way of electrode 210d is equal to the current being supplied to electrodes 210c and 210e.

Given that the return electrode 210d is receiving power from two electrodes (i.e. the transmitting electrodes 210c and 210e), it is expected that the higher current densities will result in higher temperatures being measured by temperature sensor 226d than by temperature sensors 226c and 226e. When the temperature at the return electrode 210d exceeds a predetermined level, e.g. a maximum set temperature for the transmitting electrodes 210c and 210e or a maximum set temperature for the coagulation procedure generally, the ESU controller 118 will cause the switching device 122d to interrupt the flow of current from the electrode 210d to the power return line 116 (Step 312). Interrupting the return path associated with electrode 210d eliminates the bipolar component of the combined bipolar/unipolar mode. All of the tissue coagulation energy supplied by the transmitting electrodes 210c and 210d will now be returned to the return line 116 by way of the grounding pad 104. As such, the power supply and control system 100 will continue to operate (Step 314), albeit in the unipolar mode, after the flow of energy through the return electrode 210d has been interrupted. [Note FIG. 10.]

So long as the tissue coagulation procedure has not ended and the ESU 102 remains set to the combined bipolar/unipolar mode of operation, the ESU controller 118 will cause the switching device 122d to reconnect the return electrode 210d to the power return line 116 after the temperature measured by the temperature sensor 226d has dropped to a predetermined level, such as 2° C. below in the input set temperature for the transmitting electrodes 210c and 210e or 2° C. below the input maximum set temperature for the coagulation procedure generally (Steps 316 and 318), thereby returning the power supply and control system 100 to combined bipolar/unipolar operation. Alternatively, the ESU controller 118 will cause the switching device 122d to reconnect the return electrode 210d to the power return line 116 after about 2 seconds.

It should be noted that all five of the electrodes 210a-e may be used simultaneously in the combined bipolar/unipolar mode. As illustrated in FIG. 8, electrodes 210a, 210c and 210e will function as transmitting electrodes, electrodes 210b and 210d will function as interruptible return electrodes, and the grounding pad will function as an uninterruptible return. The return paths defined in part by the electrodes 210b and 210d will be individually interruptible based on the temperatures measured by temperature sensors 226b and 226d. If, for example, the temperature at return electrode 210b exceeds a predetermined level and the temperature at return electrode 210d remains below the predetermined level, the ESU controller 118 will cause the switching device 122b to interrupt the flow of energy from the electrode 210b to the power return line 116, but allow the flow of energy from the electrode 210d to the power return line 116 to continue. Of course, the flow of current from both of the return electrodes 210b and 210d to the power return line 116 would be interrupted if necessary.

Temperature is not the only measured variable associated with tissue coagulation upon which the decision to interrupt energy flow through the return electrodes 210b and 210d may be made when operating in the combined bipolar/unipolar mode. Other measured tissue coagulation variables such as, for example, current levels, impedance levels, and the phase angle between the current and voltage, may also be employed.

Although the present inventions have been described in terms of the preferred embodiments above, numerous modifications and/or additions to the above-described preferred embodiments would be readily apparent to one skilled in the art. It is intended that the scope of the present inventions extend to all such modifications and/or additions and that the scope of the present inventions is limited solely by the claims set forth below.

I claim:

1. An apparatus for use with a probe including a plurality of probe energy transmission devices and a return device that is positionable in spaced relation to the probe, the apparatus comprising:
    a power supply;
    a power return line;
    a return device connector associated with the power return line and configured to be connected to the return device;
    a probe connector configured to be operably connected to the probe energy transmission devices; and
    a controller operable in a combined bipolar/unipolar mode where the controller connects a first probe energy transmission device to the power supply and a second probe energy transmission device to the power return line such that a portion of power supplied to the first probe energy transmission device is returned to the power return line through the second probe energy transmission device and a portion of power supplied to the first probe energy transmission device is also returned to the power return line through the return device and the return device connector, monitors a tissue coagulation variable as power is supplied to the first probe energy transmission device, and disconnects the second probe energy transmission device from the power return line while maintaining the supply of power to the first probe energy transmission device in response to a measurement of a predetermined tissue coagulation variable value.

2. An apparatus as claimed in claim 1, wherein the predetermined tissue coagulation variable comprises temperature at the second probe energy transmission device.

3. An apparatus as claimed in claim 1, wherein the controller connects a third probe energy transmission device to the power supply in the combined bipolar/unipolar mode, the second probe energy transmission device being located between the first and third probe energy transmission devices, and disconnects the second probe energy transmission device from the power return line while maintaining the supply of power to the first and third energy transmission devices in response to the measurement of a predetermined tissue coagulation variable value.

4. An apparatus as claimed in claim 1, wherein the controller reconnects the second probe energy transmission device to the power return line in response to a change in the value of the predetermined tissue coagulation variable.

5. An apparatus as claimed in claim 1, wherein the controller is operable in a bipolar mode different than the combined bipolar/unipolar mode where the controller connects the first probe energy transmission device to the power supply and the second probe energy transmission device to the power return line and all of the power that is returned to the power return line is returned through the second probe energy transmission device.

6. An apparatus as claimed in claim 1, wherein the controller is operable in a unipolar mode different than the combined bipolar/unipolar mode where the controller connects the first probe energy transmission device to the power supply and all of the power that is returned to the power return line is returned through the return device connector.

7. An apparatus as claimed in claim 1, wherein the controller controls power supplied to the first probe energy transmission device based on temperature sensed at the first probe energy transmission device.

8. A method of coagulating tissue with an electrophysiology system that includes a power supply and control apparatus, a probe with a plurality of probe energy transmission devices, and a return device that is positionable in spaced relation to the probe, the method comprising the steps of:
   transmitting energy from the power supply and control apparatus to the tissue with a first probe energy transmission device;
   returning energy from the tissue to the power supply and control apparatus through a second probe energy transmission device;
   returning energy from the tissue to the power supply and control apparatus through the return device;
   measuring a tissue coagulation variable; and
   interrupting the return of energy through the second probe energy transmission device, while continuing to transmit energy to the tissue with the first probe energy transmission device and return energy from the tissue with the return device, in response to a measurement of a predetermined tissue coagulation variable value.

9. A method as claimed in claim 8, wherein the step of transmitting energy from the power supply and control apparatus comprises transmitting energy from the power supply and control apparatus to the tissue with a first probe energy transmission device and a third probe energy transmission device, the second probe energy transmission device being located between the first and third probe energy transmission devices.

10. A method as claimed in claim 8, wherein the step of measuring a tissue coagulation variable comprises measuring temperature.

11. A method as claimed in claim 8, wherein the step of measuring a tissue coagulation variable comprises measuring temperature at the second probe energy transmission device.

12. A method as claimed in claim 8, wherein the step of interrupting the return of energy through the second probe energy transmission device comprises interrupting the return of energy through the second probe energy transmission device with a switching device.

13. A method as claimed in claim 8, further comprising the step of: reinitiating the return of energy from the tissue to the power supply and control apparatus through the second probe energy transmission device in response to a change in the value of the predetermined tissue coagulation variable.

14. A method as claimed in claim 8, further comprising the step of: controlling power to the first probe energy transmission device based on temperature measured at the first probe energy transmission device.

15. An apparatus for use with a probe including a plurality of probe energy transmission devices and a return device that is positionable in spaced relation to the probe, the apparatus comprising:
   a power supply;
   a power return line; and
   control means for connecting a first probe energy transmission device to the power supply and a second probe energy transmission device to the power return line and operable in a combined bipolar/unipolar mode such that a portion of power supplied to first probe energy transmission device is returned to the power return line through the second probe energy transmission device and a portion of power supplied to the first probe energy transmission device is also returned to the power return line through the return device and the return device connector, monitoring a tissue coagulation variable as power is supplied to the first probe energy transmission device, and disconnecting the second probe energy transmission device from the power return line while maintaining the supply of power to the first probe energy transmission device in response to a measurement of a predetermined tissue coagulation variable value.

16. An apparatus as claimed in claim 15, wherein the predetermined tissue coagulation variable comprises temperature at the second energy transmission device.

17. An apparatus as claimed in claim 15, wherein the control means reinitiates the return of energy from the tissue to the power return line through the second probe energy transmission device in response to a change in the value of the predetermined tissue coagulation variable.

18. An apparatus for use with a probe including a plurality of probe energy transmission devices and a return device that is positionable in spaced relation to the probe, the apparatus comprising:
   a power supply;
   a power return line; and
   a controller associated with the power supply and power return line, the controller being operable in a unipolar mode and a combined bipolar/unipolar mode and configured to switch from the combined bipolar/unipolar mode to the unipolar mode in response to a measurement of a predetermined tissue coagulation variable value.

19. An apparatus as claimed in claim 18, wherein the controller connects at least one probe energy transmission device to the power return line in the combined bipolar/unipolar mode and disconnects the at least one probe energy transmission device from the power return line in response to the measurement of a predetermined tissue coagulation variable value.

20. An apparatus as claimed in claim 18, wherein the predetermined tissue coagulation variable comprises temperature at a probe energy transmission device that is connected to the power return line.

21. An apparatus as claimed in claim 18, wherein the controller connects first and second probe energy transmission devices to the power supply and connects a third probe energy transmission device, located between the first and second probe energy transmission devices, to the power return line in the combined bipolar/unipolar mode.

22. An apparatus as claimed in claim 21, wherein the controller controls power to the first and second probe energy transmission devices based on temperatures measured at the first and second probe energy transmission devices in the combined bipolar/unipolar mode.

23. An apparatus as claimed in claim 22, wherein the controller disconnects the third probe energy transmission device from the power return line when the controller switches from the combined bipolar/unipolar mode to the unipolar mode.

24. An apparatus as claimed in claim 18, wherein the controller is configured to switch back to the combined bipolar/unipolar mode in response to a change in the value of the predetermined tissue coagulation variable.

25. A method of coagulating tissue with an electrophysiology system that includes a power supply and control apparatus, a probe with a plurality of probe energy transmission devices, and a return device that is positionable in spaced relation to the probe, the method comprising the steps of:
    operating the system in a combined bipolar/unipolar mode; measuring a tissue coagulation variable; and
    switching from the combined bipolar/unipolar mode to a unipolar mode in response to a measurement of a predetermined tissue coagulation variable value.

26. A method as claimed in claim 25, wherein the step of operating the system in a combined bipolar/unipolar mode comprises connecting a first probe energy transmission devices to the power supply and connecting a second probe energy transmission device to the power return line.

27. A method as claimed in claim 26, wherein the step of measuring a tissue coagulation variable comprises measuring temperature; and the step of switching from the combined bipolar/unipolar mode to a unipolar mode comprises switching from the combined bipolar/unipolar mode to a unipolar mode in response to a measurement of a predetermined temperature at the second probe energy transmission device.

28. A method as claimed in claim 25, wherein the step of operating the system in a combined bipolar/unipolar mode comprises connecting first and second probe energy transmission devices to the power supply and connecting a third probe energy transmission device, located between the first and second probe energy transmission devices, to the power return line.

29. A method as claimed in claim 28, wherein the step of measuring a tissue coagulation variable comprises measuring temperature; and the step of switching from the combined bipolar/unipolar mode to a unipolar mode comprises switching from the combined bipolar/unipolar mode to a unipolar mode in response to a measurement of a predetermined temperature at the third probe energy transmission device.

30. A method as claimed in claim 25, further comprising the step of: switching back to the combined bipolar/unipolar mode in response to a change in the value of the predetermined tissue coagulation variable.

31. An apparatus for use with a probe operable in a combined bipolar/unipolar mode, the apparatus including a plurality of probe energy transmission devices and a return device that is positionable in spaced relation to the probe, the apparatus comprising:
    a power supply;
    a power return line;
    a return device connector;
    an uninterruptible connection between the power return line and the return line connector;
    a probe connector operably connected to the power supply and associated with the probe that is operable in the combined bipolar/unipolar mode; and
    an interruptible connection between the probe connector and the power return line.

* * * * *